(12) United States Patent
Nadal

(10) Patent No.: US 6,302,891 B1
(45) Date of Patent: *Oct. 16, 2001

(54) SYSTEM FOR REPAIRING AN ANATOMICAL CANAL BY MEANS OF AN IMPLANT WITH A PROGRESSIVE OPENING

(75) Inventor: Guy Nadal, Poitiers (FR)

(73) Assignee: B. Braun Celsa (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/075,184

(22) Filed: May 11, 1998

(30) Foreign Application Priority Data

May 12, 1997 (FR) .................................................. 97 05783

(51) Int. Cl.⁷ ................................ A61F 11/00; A61F 2/06
(52) U.S. Cl. ......................... 606/108; 623/1.11; 606/194
(58) Field of Search ................................. 623/1, 12, 1.11, 623/1.12; 606/108, 192, 194, 195

(56) References Cited

U.S. PATENT DOCUMENTS

| 4,878,906 | * | 11/1989 | Lindemann et al. ................. | 606/108 |
| 5,405,378 | | 4/1995 | Strecker . | |
| 5,776,141 | * | 7/1998 | Klein et al. ........................... | 606/108 |
| 5,776,142 | * | 7/1998 | Gunderson ............................... | 623/1 |
| 5,782,838 | * | 7/1998 | Beyar et al. ......................... | 606/108 |

FOREIGN PATENT DOCUMENTS

| 423916 | * | 4/1991 | (EP) ........................................ | 623/1 |
| 9501761 | | 1/1995 | (WO) . | |
| 9618361 | | 6/1996 | (WO) . | |

* cited by examiner

*Primary Examiner*—Bruce Snow
(74) *Attorney, Agent, or Firm*—Rothwell, Figg, Ernst & Manbeck

(57) ABSTRACT

The system-for repairing an anatomic duct comprises an implant having a tubular body adapted to be radially expanded, once the implant is arranged in the duct and also a device for installing the implant in said duct. The device comprises a tie for maintaining the body in a restricted configuration, for the implantation thereof in the duct, and means for releasing the tie in order to allow the implant to radially expand.

8 Claims, 8 Drawing Sheets

FIG. 8   FIG. 9   FIG. 10

FIG_11

FIG_12

FIG_15a

FIG. 17

SYSTEM FOR REPAIRING AN ANATOMICAL CANAL BY MEANS OF AN IMPLANT WITH A PROGRESSIVE OPENING

FIELD OF THE INVENTION

The invention concerns a system or device for repairing an anatomical canal, or duct, in which a fluid circulates.

In particular, it is a matter of repairing a blood vessel.

DESCRIPTION OF THE BACKGROUND ART

The vessel "to be repaired" may typically be affected by one or more aneurisms or by degeneration necessitating the installation of tubing intended to channel the blood in the damaged portion(s), thus preventing the blood pressure from being allowed to be applied to the weakened walls of the vessel.

Up to the present, numerous vascular implants for the treatment of aneurisms have been proposed.

For several years, the installation of these implants by the percutaneous endoluminal route has been favoured.

Among these existing systems, WO-A-96/18361 proposes in particular a system comprising:

an implant having a body suitable for channelling the fluid in question along a single or branched tube extending generally along a major axis of the implant, at least in one configuration of the latter, which latter has a first configuration in order to be contained inside a flexible sheath, for the purpose of implantation in the canal, or a second configuration, once the implant is arranged in the canal outside the sheath, the first configuration having a radial dimension overall with respect to the said major axis which is smaller than the second configuration and the said body having a length along that axis;

a device for installing the implant in the canal, the device comprising:
said flexible sheath,
at least one retaining tie, to maintain the body substantially in the first configuration of the implant,
and means for releasing the tie, in order to allow the implant to pass from its first to its second configuration.

WO-A-96/18361 provides for the combined use of ties for retaining the body of the implant in the "radially restricted" state of the implant and means for releasing the said ties, making it possible to control both the introduction of the body into the installation sheath and the actual step of implantation of the implant in the receiving anatomical canal.

But in reality, the action of the ties operates on two radially deployable tubular stents (or expanders), respectively arranged in "upper" (distal) and "lower" (proximal) portions of the implant.

However, between these two "upper" and "lower" levels, the release thread used to allow the stents to expand radially passes inside a central catheter round which the implant has been arranged, inside the implantation sheath.

Moreover, other threads or filaments are associated with the release and retaining means already mentioned, which makes the solution of WO-A-96/18361 complicated to carry out and difficult to use.

FIGS. 1 to 5 provide some exemplary embodiments of prior art vascular implants intended for the treatment of aneurisms, it being stated that practically all the existing configurations on this subject could be used, whether it is a question of an implant with armature (stent) which is self-expanding (that is to say, naturally having the capacity of deforming resiliently in a radial direction from a first, constricted diameter to a second, expanded diameter) or of an implant with an armature radially deployable by the effect of an internal force that can be created by means of an inflatable balloon which, when the time comes, is inflated inside the implant (as in U.S. Pat. No. 4,733,665, for example).

Typically, the sleeve or body 3 is a woven or non-woven fabric without inherent mechanical strength. In its radially deployed form in FIG. 1, it is in the form of a cylindrical tube of circular cross-section and having its axis 1a coinciding with that of the implant 1. It has a continuous wall.

Figures 1, 2, 3, 4, 5:
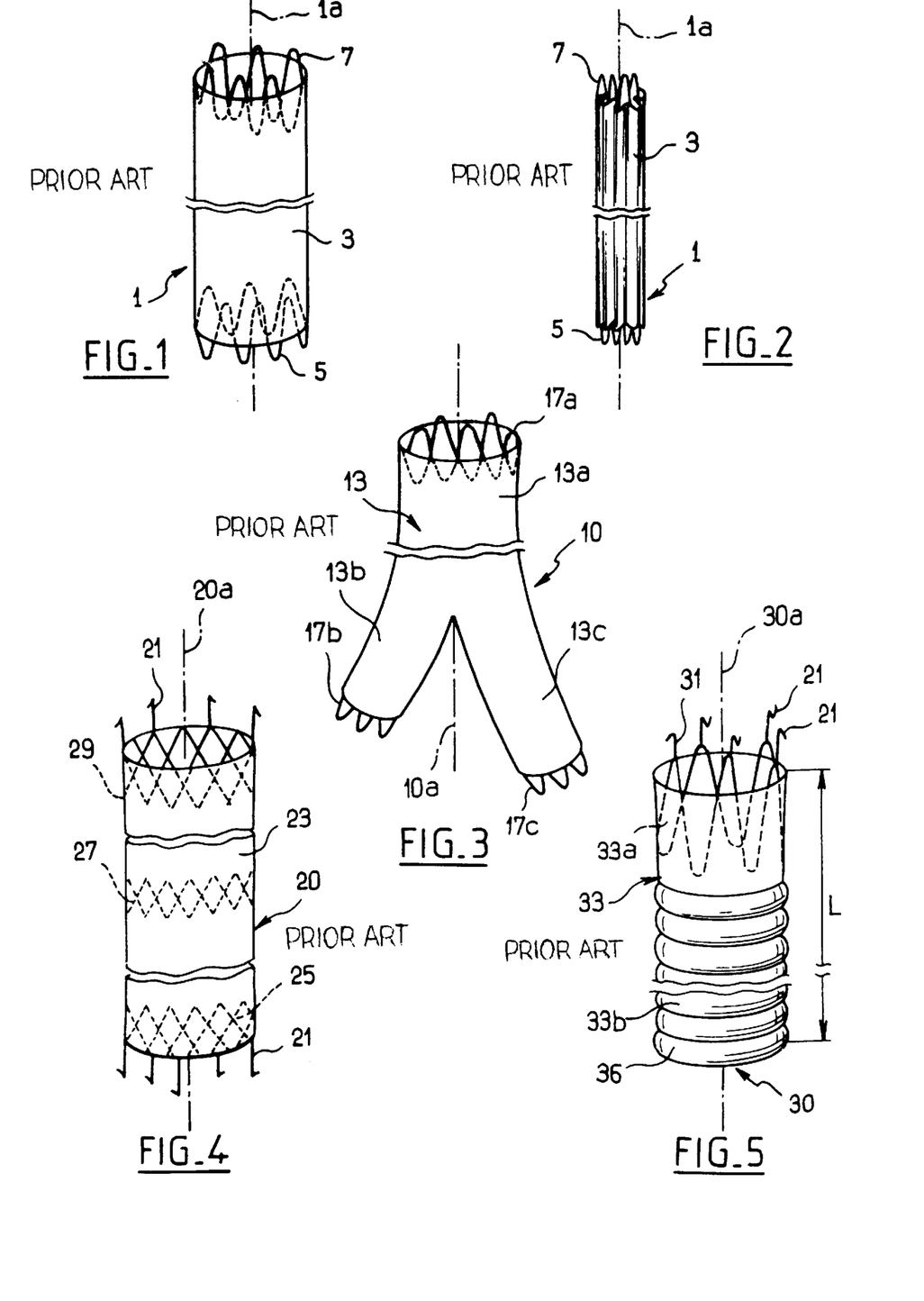
FIGS. 1 to 5 show diagrammatically alternative various prior art vascular implants.

An intermediate portion of the sleeve 3 might possibly be embossed in order to resist folding or kinking.

Axially, the sleeve 3 may have a length of between approximately 6 cm and 16 cm, with a diameter in its "radially deployed" state in FIG. 1 of between approximately 5 mm (iliac implantation) and 45 mm (aortic implantation). Its wall structure may be produced from polyethylene terephthalate (PET), or more generally from polyester or PTFE, with a wall thickness of the order of 0.10 mm to 0.80 mm.

For its implantation by means of a small diameter sheath (in particular by the percutaneous endoluminal route) and in order to ensure the application of the implant against the wall of the receiving canal, two tubular spring means 5, 7 have been provided, respectively arranged towards the proximal and distal ends of the sleeve 3. In the present instance these are two stents in the form of zigzags each defining a ring closed on itself, in the manner provided for in EP-A-177 330 or in WO-A-96/18361. To produce these stents, a metal wire (for example made of stainless steel) may be used which may have a diameter of the order of 0.5 mm, in order to produce a ring which is naturally radially expansible to change between a constricted ring diameter (FIG. 2) of approximately 2 mm to 9 mm and the naturally expanded diameter already indicated (FIG. 1).

In the radially constricted position in FIG. 2, it will be noted that the sleeve 3 has longitudinal folds.

In FIG. 3 there can be seen an implant 10 of the same type as that in FIGS. 1 and 2, except for the principal difference that the implant 10 is bifurcated. For this purpose the sleeve here identified by 13 has a principal section 13a which branches into two limbs 13b, 13c, one of which may be shorter than the other, imparting to the deployed tube 13a general inverted Y-shape.

At the free end of each of the sections 13a, 13b, 13c, an "expander" respectively 17a, 17b, 17c, shaped like the stents 5, 7, has been at least partially slid inside the corresponding section to which it can be fastened by any means, such as suture ties or clips.

In order to install the implant 10 in its receiving duct, by way of a device for implantation by the endoluminal route, each of the expanders is restricted radially and the two limbs 13b, 13c are applied one against the other so as to arrange the whole substantially along the general axis 10a.

In FIG. 4, the implant 20 is again in the form of a single tube with longitudinal axis 20a. But in the present instance the armature for radial deployment of the sleeve 23 (of the same type as the sleeve 3) is constituted by three tubes 25, 27, 29, each formed of a plurality of intersecting elongate elements consisting of a plurality of thin bars fixed to one another at their crossing points, so as to form a sort of grid radially deformable by the effect of an internal force (balloon or equivalent; see U.S. Pat. No. 4,733,665).

In FIG. 4, there have also been shown at 21 attachment hooks fixed respectively to the proximal section 25 and distal section 29 of the armature in order to hook the implant 20 into the wall of its receiving canal, in the radially deployed position. Such attachment hooks may of course be provided on the variants in FIGS. 1, 3 or 5.

In FIG. 5 only, there is shown another variant of an implant for aneurism, 30. The illustration shows diagrammatically an implant as disclosed in EP-A-836 452.

It will thus be observed that the vascular implant 30 comprises a proximal tubular armature 31 having one or more levels of filamentary winding in zigzags. This metallic armature is self-expanding, so that in the absence of radial constraint, it causes the distal portion 33a of the sleeve 33 which extends round it to be deployed radially. This first portion 33a is, like the sleeve 3, devoid of inherent mechanical strength, unlike the second portion 33b. This portion 33b, which axially extends the first, has naturally, in effect, a radially deployed tubular shape, in the manner of surgical vessel substitutes (see for example WO-A-88/06026 or U.S. Pat. No. 3,986,828).

The portion 33b is preferably impermeable to blood and is provided to be anastomosed to the receiving vessel in question, towards its proximal free end 36.

There is no stent (or equivalent means of radial deployment) with regard to the essential part at least of this anastomosable portion 33b which may be embossed and be manufactured, for example, from Dacron (registered trademark).

BRIEF DESCRIPTION OF THE INVENTION

An object of the invention is to propose a solution making possible in particular to control the installation conditions with regard to the moment when the tubular body of the implant opens in its receiving canal, while limiting the risks that the body might be poorly positioned in its implantation sheath.

In other words, the invention proposes to provide a solution to the rigorous conditions both for the installing of the implant (and in particular of its "tubular" body) in the installation sheath, and for the radial opening when the body of the implant should therefore be applied at least locally against the wall of its receiving canal.

For this, the solution of the invention consists in that the repair system mentioned above is such that the tie(s) for retaining the body of the implant extend(s) round at least a major portion of the length of the body, in order then to maintain it substantially in the said first configuration of the implant, over this major portion.

Thus, if one does not of course exclude in the invention the use of one or more clamping ties for maintaining in the first (radially "restricted") configuration the means which can be used on the implant to apply the tubular body against the inner wall of the receiving canal (stents), then, in particular, both the installation and the conditions for radial opening of the body of this implant are optimised.

In this regard, a complementary characteristic provides that the tie(s) in question will enlace the body, in the sheath, forming, with each other or in co-operation with the release means, a series of releasable interlacings, over at least the said "major portion" of the body.

Thus, the ties in question will surround the body several times, clamping it, preferably on an inner catheter round which the whole of the implant will have been previously arranged.

In order to control, in particular, the correct opening of the body, a complementary characteristic of the invention provides that the release means and the interlacings will co-operate preferably together so that the interlacings are released progressively by the release means, one after the other.

This is particularly of interest inside tortuous vessels or during the installation of a bifurcated implant, thus allowing the practician first to optimise the positioning of the implant in its receiving canal before opening it in a second step.

It is also with this in mind that a complementary characteristic of the invention provides that, advantageously, the release means will be connected to the tie(s) at one end of the ligature produced, so that its release works, from that end, only in one direction.

In fact, it is then substantially starting from one end of the body that the opening of the latter can be initiated (in particular from its distal end, in the direction of its proximal end), which will moreover simplify the practical conditions for producing the "tie(s)/release means" connection.

Concerning the manner in which the body is retained by the tie(s), a first solution proposes that the tie(s) define(s) a succession of loops essentially holding onto one another, being spaced out at least on the said major portion of the length of the body, in order to form a chain.

A second solution consists in providing for the use, as release means, of at least one elongate element, which is flexible but has a rigidity greater than that of the ties and which extends at least over the said major portion of the length of the tubular body, the tie(s) passing substantially in a "hairpin" shape round the elongate element, periodically on one side and on the other of the latter, being spaced out at least over the said major portion of the length of the body, so as to form a releasable knot in the vicinity of at least one end of connection between the elongate element in question and the tie under consideration, making it possible to release the (each) tie by means of action on the knot and the said release means which ensure the escape of the first from the second.

If this solution is employed, another characteristic of the invention moreover advises that the said releasable knot should be formed towards the distal end of the elongate element, which will itself extent towards the distal end of the body (and therefore of the implant), in such a way that the knot in question is capable of escaping from the element at the moment when the latter is pulled towards the rear, from outside the body of the patient (proximal end of the installation means), thus progressively releasing the successive "hairpins" as the said element is withdrawn.

A more detailed description of the invention will now be provided with reference to the accompanying drawings, in which:

BRIEF DESCRIPTION OF THE FIGURES

FIGS. 6, 7, 8, 9 and 13 essentially show an implantation device that can be used to introduce one of the above implants into its implantation canal, FIGS. 7 and 13 illustrating the device in place and showing the ties that are characteristic of the invention, FIG. 9 is an enlarged detail view of FIG. 8, at the point identified by IX in FIG. 8, and shows the flexible threads which are characteristic of the invention, FIG. 14 shows the implant in place in its receiving canal.

DETAILED DESCRIPTION OF THE INVENTION

Figures 6, 7:
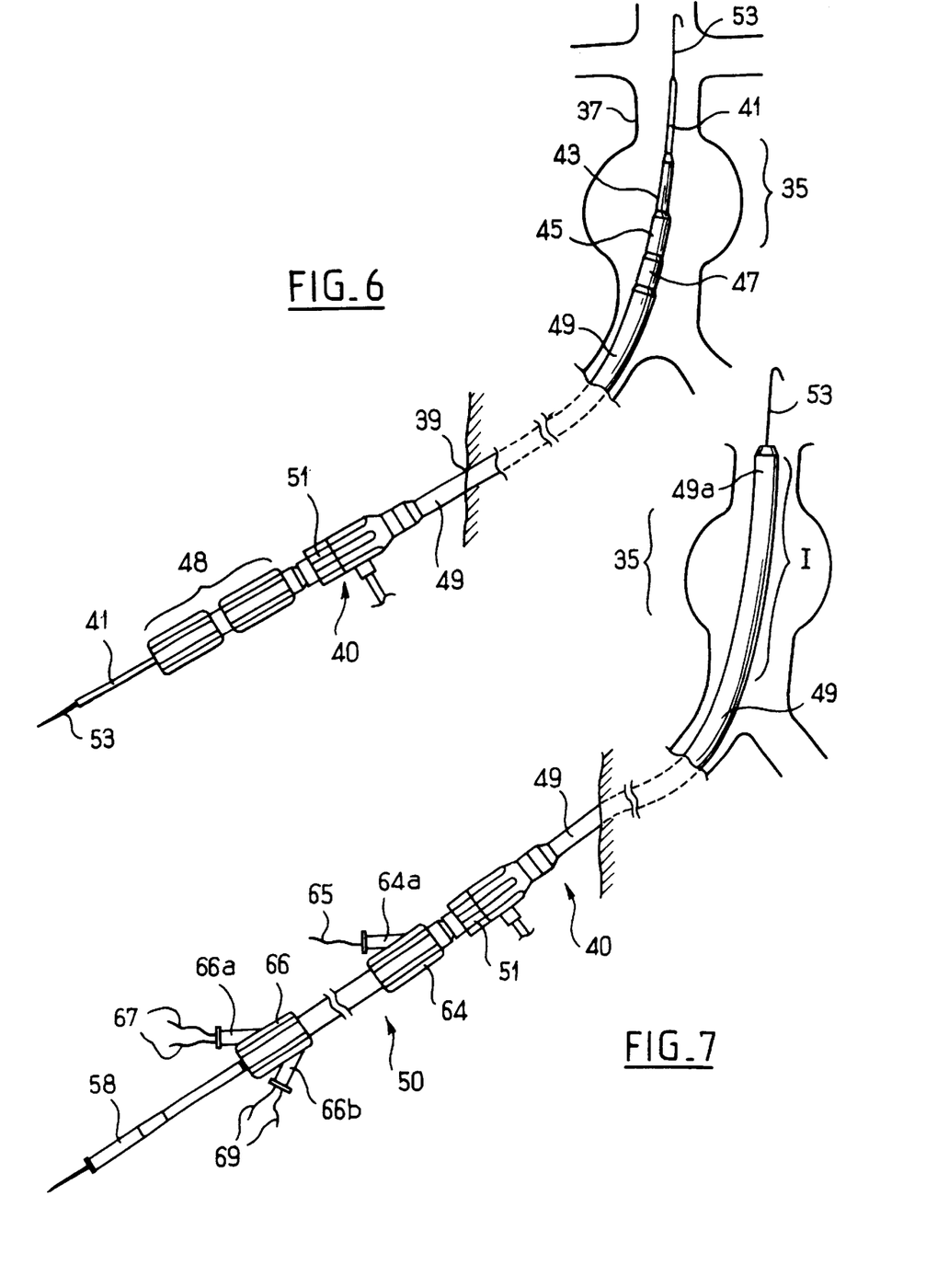
Figure 17:
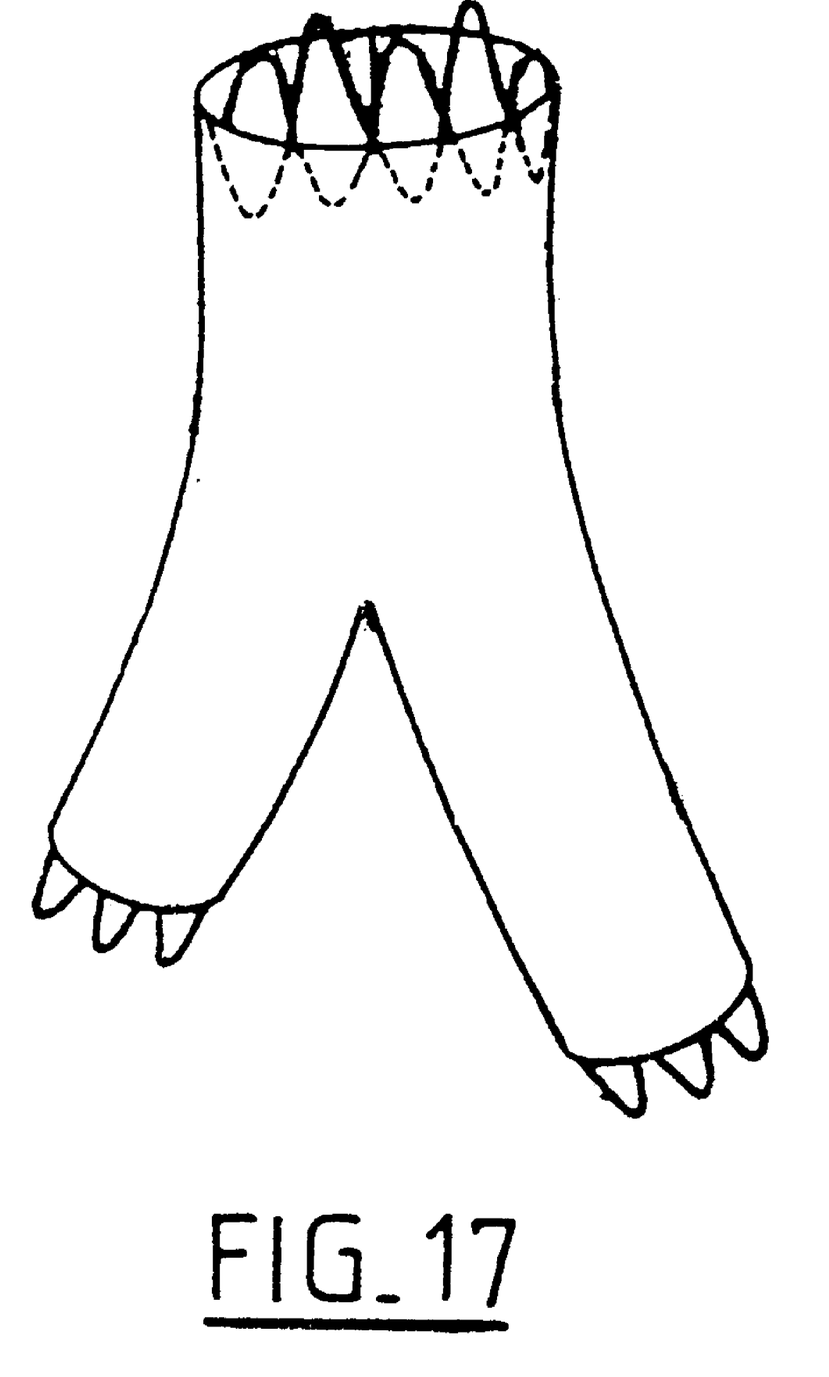
FIG. 17 shows a branched tube implant inserted by the system of the present invention.

With reference to FIGS. 6 and onwards, the installation of one of these implants described above, for example that in FIG. 3, such as a branched tube implant shown in FIG. 17, will now be dealt with from the standpoint of the treatment of an aortic aneurism 35.

For the sake of clarity, only the particular case of such a vascular implant is presently dealt with even if the invention could be concerned with other ailments and anatomical canals.

The practician can effect implantation by an initial percutaneous route, or by vascular stripping.

Let it be assumed that implantation in the aorta 37 by the percutaneous route has been employed, for example with a femoral approach through the right iliac artery.

After having incised through the skin at 39, the practician can use first a first implantation assembly 40 such as is illustrated in FIG. 6, comprising a flexible dilator 41 round which a series of flexible sheaths 43, 45, 47, 49 of increasing diameter, with blunt distal end, are arranged in succession.

The outer sheath 49 is provided with a proximal end-piece with internal valve, 51.

The inner sheaths 43, 45, 47 are integral with the proximal connection 48.

A conventional guide wire 53 is first slid through the incision and through the right iliac, into the aorta. Along the guide wire there is then slid the dilator 41 round which the sheaths 43, 45, 47 and 49 . . are then introduced.

Once the sheath 49 is correctly positioned, with its distal end 49a slightly beyond the aneurism 35, the dilator 41 and the intermediate sheaths 43, 45, 37 are withdrawn, as well as the guide wire 53.

Figures 8, 9:
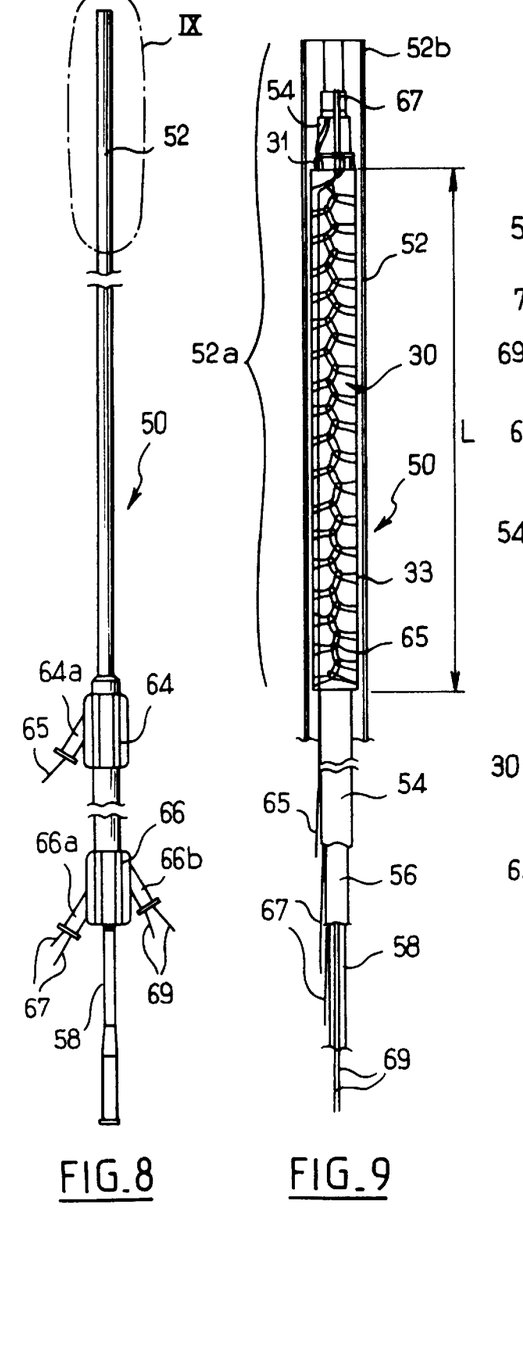

There is then slid inside the sheath 49 a second installation assembly 50, as shown in FIG. 7 and which is distinguished more clearly in FIGS. 8 and 9.

The assembly 50 comprises an outer sheath 52 capable of being slid inside the sheath 49 and which, over at least the essential part of its length, contains three concentric tubes or catheters identified successively (from the largest to the smallest) by 54, 56 and 58 in FIG. 9, FIG. 8 showing that the central catheter 58 is longer than the sheath 52 and the other intermediate catheters (54 and 56), respectively provided with a proximal end-piece 64, 66 that can be screwed. It should be noted that the end-piece 64 has a lateral outlet 64a through which there can be seen emerging a flexible thread 65, while the end-piece 66 has two lateral outlets 66a and 66b through which emerge the two opposed ends of two other flexible threads, respectively 67 and 69, the usefulness of which will be understood. The threads may be of polyester or Nylon (registered trademark), such as suture threads.

Figure 10:
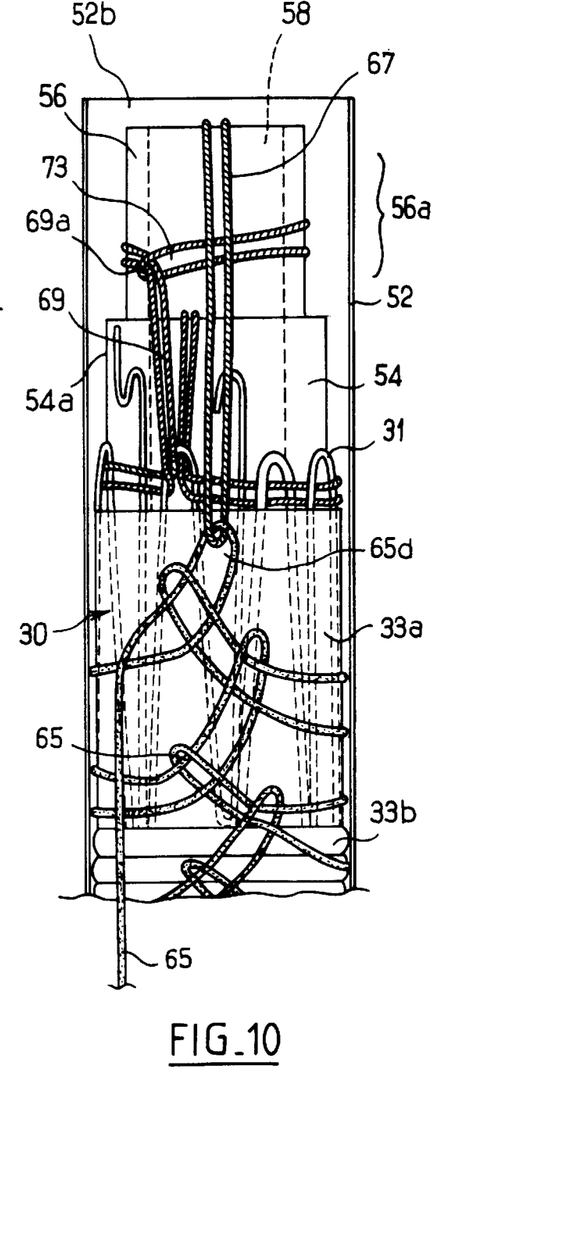
FIG. 10 is an even more enlarged view of the upper part in FIG. 9, FIGS. 11 and 12 show (in an enlarged detail view in the case of FIG. 12) the lacing or knotting principle employed for the body of the implant in FIGS. 9 and 10, which is a characteristic of the invention.

Inside the sheath 52, and more particularly in its distal area 52a close to its free distal end 52b, the implant 30 has been pre-loaded (see FIGS. 9 and 10).

More precisely, the implant has been placed in position between the sheath 52 and the catheter 54, with its distal sleeve part 33a supported by the armature 31 ready to emerge first.

In order to maintain the implant 30, and in particular its body forming a sleeve 33, inside the sheath 52 (which typicaly has an inside diameter D of the order of 2 mm to 9 mm), the thread 65 which has already been mentioned has been passed in the manner of a clamping tie round at least the essential part of the axial length L of the body 33.

This tie (but there could also be several of them) has the first function of fixing, inside the sheath 52, the position of the sleeve 33 which is thus placed optimally in its "radially constricted" state, thus avoiding bad folds and other inappropriate states.

Thus, the tie 65 extends at least round the portion of sheath which is not supported by the armature 31, the more so since in the present instance the portion in question (33b) naturally has a tendency to open radially and it is therefore necessary to constrain it so that, correctly folded, it occupies a sufficiently reduced radial space to be able to be introduced inside the sheath 52.

In FIGS. 9, 10, 11 and 15, the tie 65 also extends however round the distal area 33a, that is to say, over the stent 31, over substantially the whole of the axial length of the implant 30.

Figure 15:
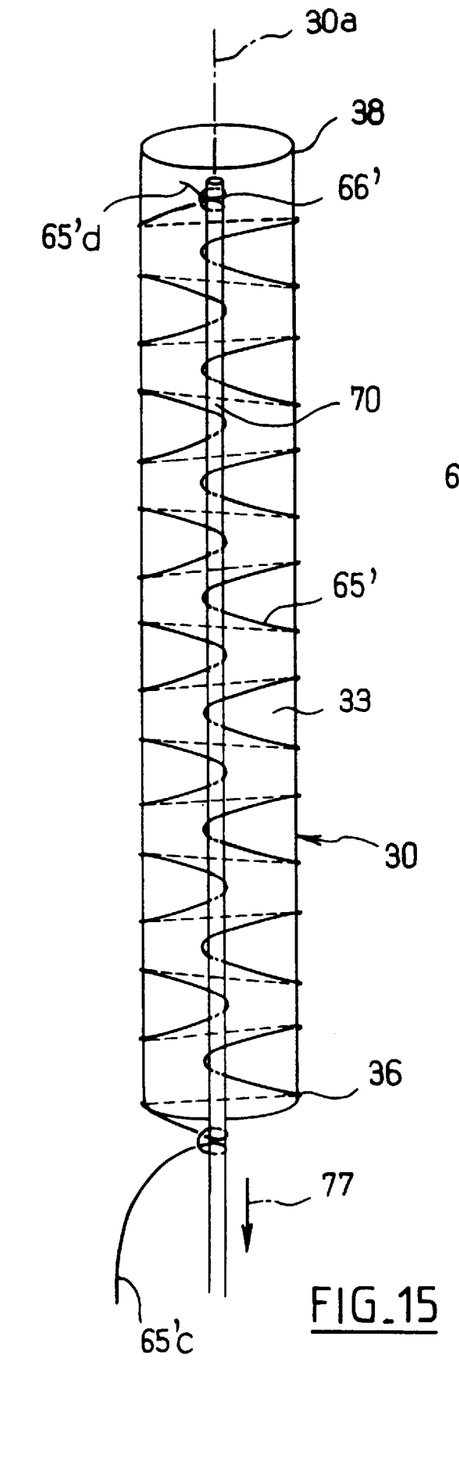
FIGS. 15 and 16 show (in an enlarged detail view in the case of FIG. 16) an alternative form of knotting for enlacing the implant body, and FIG. 15a further describes the flattened nature of the cross-section of the elongated member in FIG. 15.
Figure 15A:
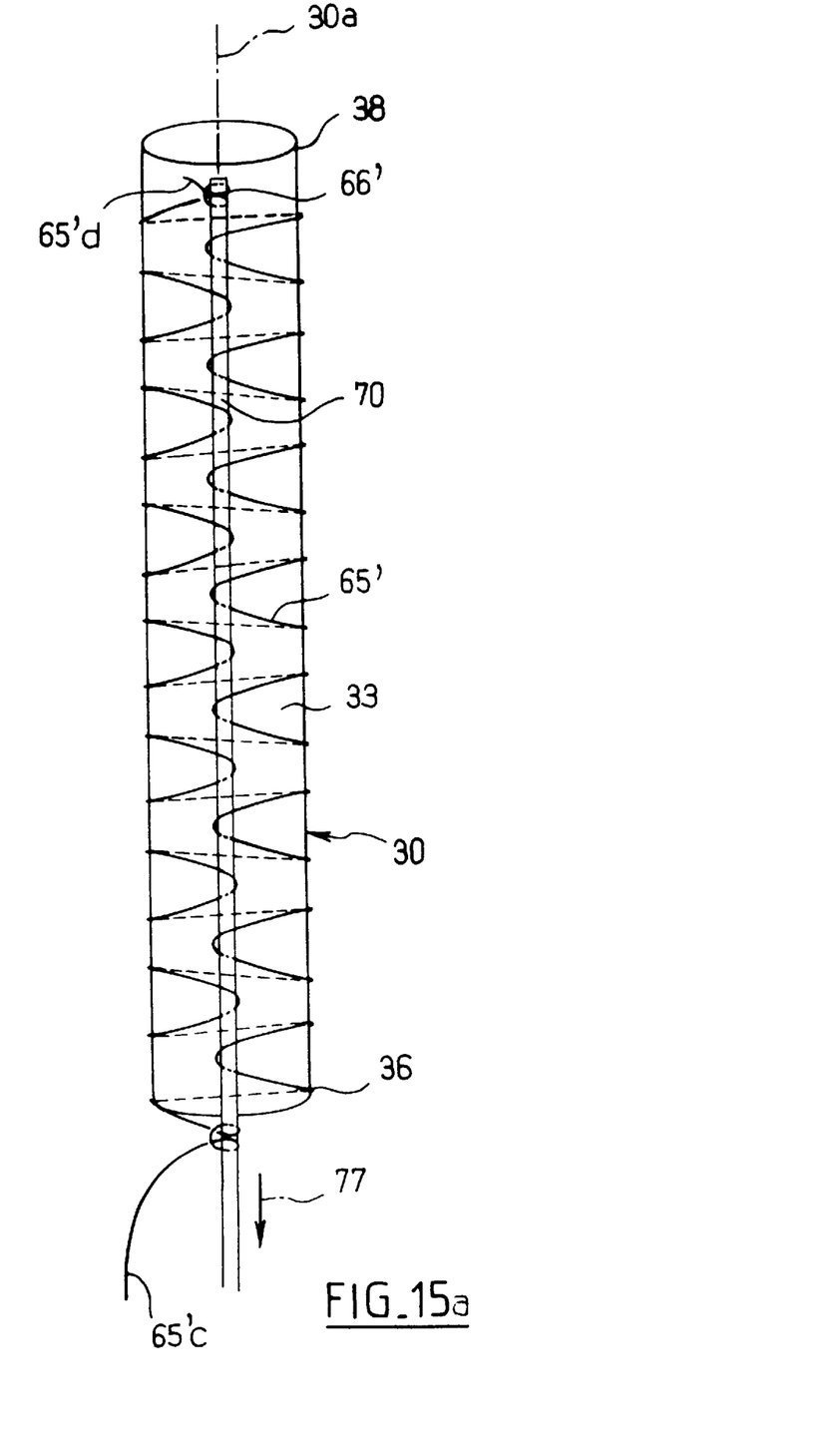
Figure 16:
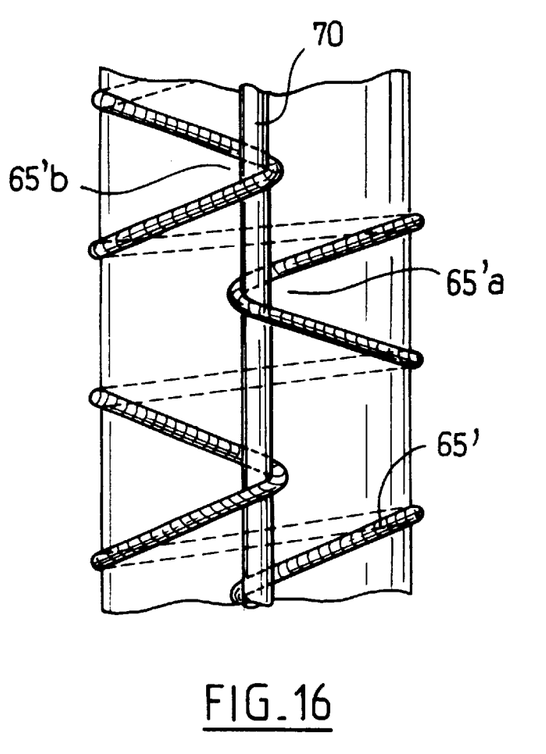

In order to effect radial clamping round the sleeve, the tie enlaces it by forming a series of regular interlacings along this body, the interlacings being releasable, in the present instance by an adjacent release means which may be in different forms, such as the flexible thread 67 of FIGS. 9 to 12 or the more rigid rod 70 of FIGS. 15 and 16.

Figure 11:
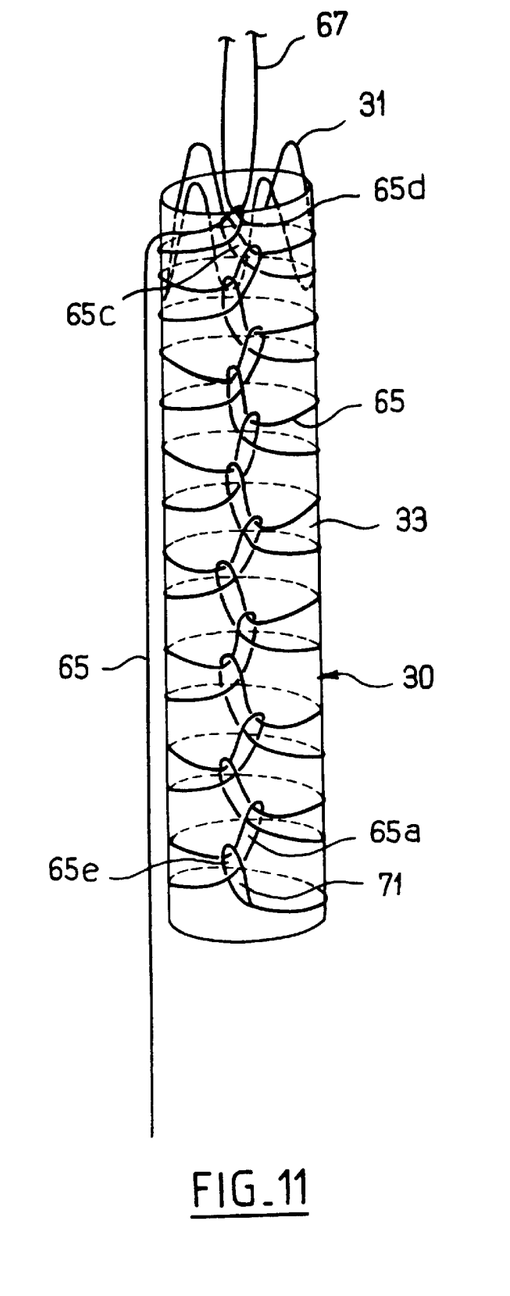
Figure 12:
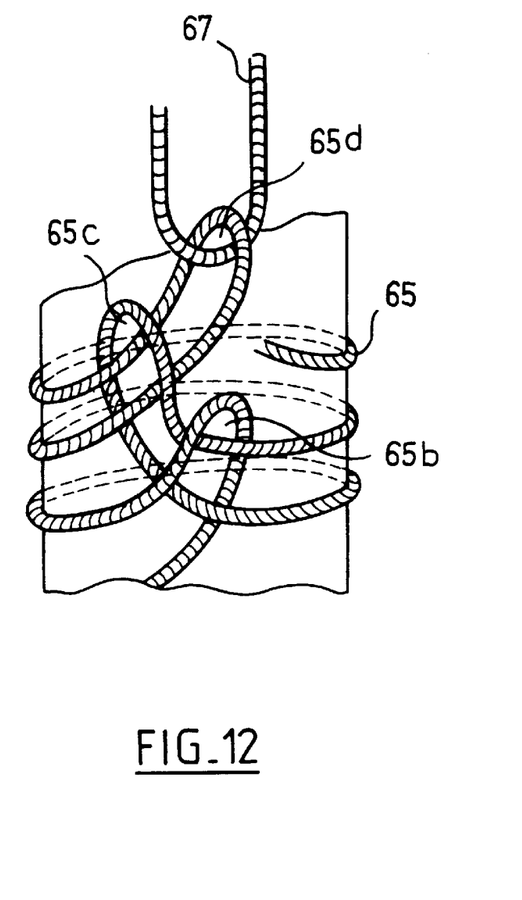

In the version in FIGS. 9 to 13, the tie 65 has been wound in such a way as to define a series of loops, three of which have been identified by 65b, 65c, 65d in FIG. 12. These loops all hold on to one another, as far as the last but one (65c) and are spaced along the body to be retained in order to form a chain.

In order to hold the thread on the same side as its first loop 65a, the free end of the closest thread 65e has been previously knotted in order to keep a ring 71 inside which the first loop shape 65a has been passed.

Beyond the last loop 65d, it can still be seen in FIG. 11 that the thread 65 passes back along the body and then, afterwards, along the catheters 52, 54 (FIG. 9) to reemerge through the lateral branching 64a in FIG. 8.

With regard to the retention of this last (distal) loop 65d, FIG. 10 in particular shows that it can be effected by the passage of the tie 67 through it, the two strands of the thread 67 thus folded back then coming backwards in order to pass between the catheters 56 and 58 to reemerge through the lateral access 66a of FIG. 8.

In the example of FIGS. 9 and 10, a choice has been made also to maintain the stent 31 clamped externally against the catheter 54.

For this purpose, the thread 69 has been first doubled back on itself, then its bent end 69a slipped between the catheters 54 and 56, to re-emerge at the distal end 54a of the catheter 54 in order then to pass "over and under" in the zigzags of the stent 31, in order to terminate round the emerging distal portion 56a of the catheter 56, forming the running knot 73, the two joined strands of thread 69 themselves reemerging through the lateral branching 66b of FIG. 8.

Once these elements have thus been placed in position, the sheath 52 will be slid inside the sheath 49 (of suitable diameter), so as to reproduce the situation in FIG. 7.

The implant 30 is then situated facing the location I marked on this Figure. And the end-piece 64 is then butted against the end-piece with valve 51.

Figures 13, 14:
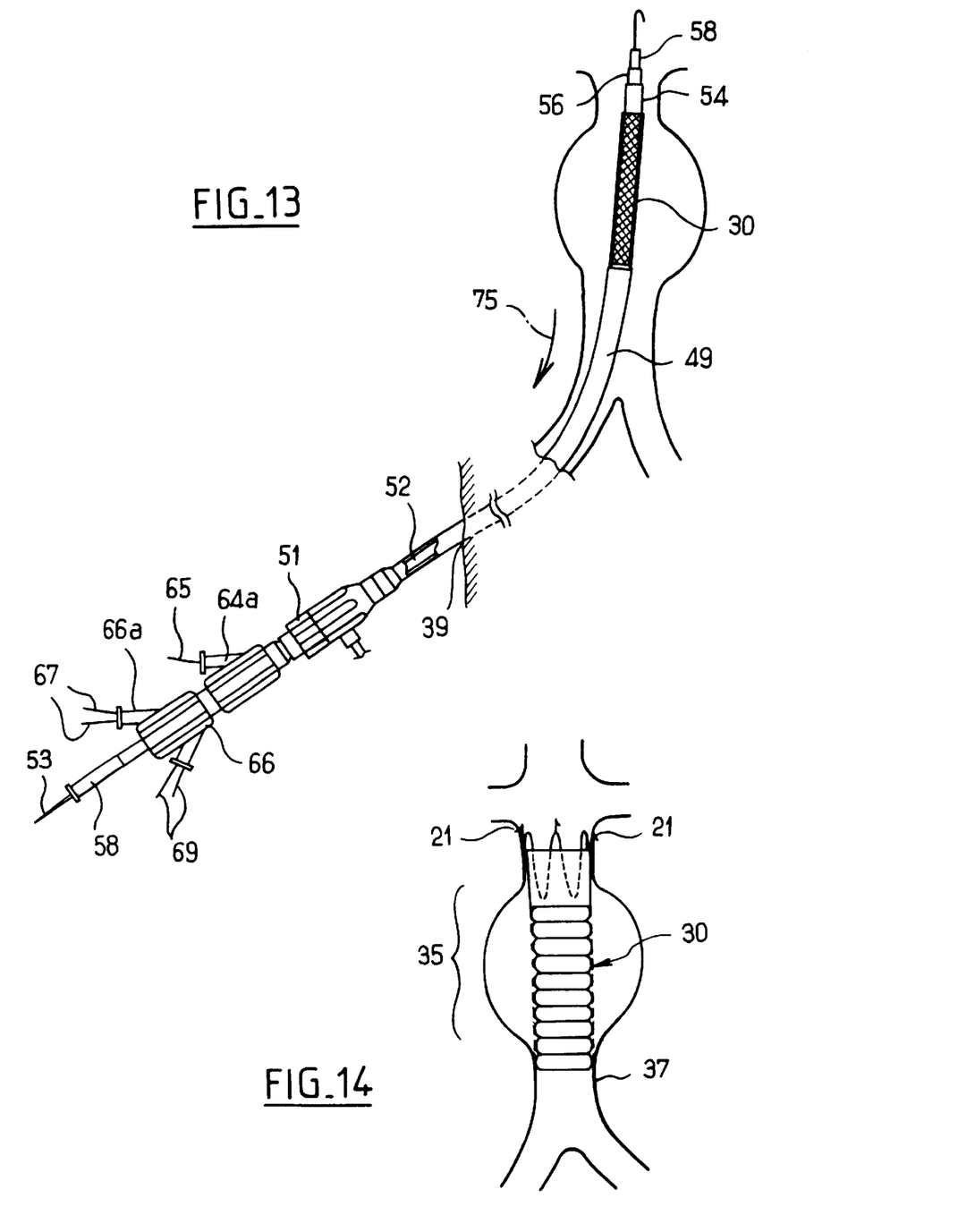

While keeping fixed in position the catheter 58 and the end-piece 66, carrying the catheters 54, 56, the practician then pulls towards the rear (in the direction of the arrow 75 in FIG. 13) the assembly formed by the sheaths 49 and 52, so as to arrive at the situation in FIG. 13 which shows the implant 30 still arranged with its ties and release means round the more central catheters 54, 56 and 58.

By pulling on one of the two strands of the thread 67 emerging through 66a, the thread can then be withdrawn, thus releasing from any retention the distal loop 65d (see FIG. 10) and similarly the retention of the loops in a chain formed by the thread 65.

By pulling on the end of this thread which re-emerges through 64a (FIG. 8), the practician then releases from its radial retention at least the body of the implant.

If the body comprises the portion 33b already mentioned, the latter therefore opens radially in order to reassume its tubular shape in FIG. 5.

Should the practician fear that the withdrawal of the catheter 56 which he is now going to carry out might result, by way of the catheter 54, in an unwanted movement, in particular an axial movement, of the still clamped stent 31, provision may be made to provide a movement of relative axial translation between the catheters 54 and 56 (by additionally dividing in two the end-piece 66 for example).

Whatever the case may be, it is necessary for the practician, by withdrawal towards the rear (arrow 75), to obtain a recoil of the catheter 56 permitting the part of the thread 69 surrounding it to escape, thus releasing the running knot 73. It is then possible, for example, to pull on one of the two ends of the thread 69 emerging through 66b in order to withdraw this thread completely, thus releasing the stent 31 which then expands radially to be applied against the facing wall of the vessel with its hooks, which anchor themselves in this wall.

It is then sufficient for the practician to withdraw completely the catheters 54, 56 and 58, after which the initial route 39 (and in particular the incision) can be closed again, for example by means of sutures. The implant 30 is then deployed in the vessel, with its hooks 21 anchored, as in FIG. 14.

As an alternative to the knotting solution in FIGS. 11 and 12, that in FIGS. 15 and 16 may be employed.

In FIG. 15, it will be noted that although there is still a flexible thread marked 65' for radially maintaining at least the body 33 of the implant 30 shown diagrammatically again, neither the release thread 67 nor the thread 69 for radial retention of the armature of the implant is to be found any longer.

In place thereof, there will be observed the elongate element 70 which extends parallel to the axis 30a of the implant, on the outside of its body 33. In practice, this elongate element 70 may be a metal or plastic rod, of preferably flattened cross-section, in order to be less bulky radially and to prevent it from forming a coil under the shear stresses brought about by the "alternating" passage of the tie 65' round the said bar 70.

Although it is difficult to describe (while including the equivalents) the manner in which the tie 65' enlaces the body 33, while passing periodically round the flat bar 70, it may be considered that after having been knotted, in the intermediate part, on the same side as the proximal end 36 of the implant (intended to emerge last from the installation sheath 52 inside the implantation canal), while leaving one of its strands (65'c) free, the tie 65' is wound in a portion of a helix round the body 33, with a change in the direction of winding of the helix each time it passes round the bar 70 (see a change in pitch of this helix). It may also be considered that the tie 65' thus defines, owing to the successive passages with a change of orientation round the rod 70, a series of hairpins 65', 65'b, . . . etc, alternately to the left and to the right of the bar and spaced out axially, until at its free end 65'd the tie forms an untightened knot 66' round the distal end 70b of the element 70 which therefore extends over the desired length, from outside the body of the patient in the direction of the distal end 38 of the implant In order to liberate the latter, or at least its channelling body 33, the implant then clamped by the tie 65' itself maintained in this situation of radial retention by the rod 70, is placed in the area I of FIG. 7. A proximal portion of the rod 70 reemerges sufficiently from the body of the patient, through the installation assembly already described, in order to be able to be maneuvered by the practician.

The latter, when the moment arrives, pulls the rod 70 towards the rear in the direction of the arrow 77 of FIG. 15. The knot 66' then escapes from the distal end of the rod 70, a priori by coming undone, thus allowing the implant (or at least its body 33, or equivalent) to be able to open naturally (or to be opened by a stent), progressively and without any stress created on it.

The practician recovers both the tie 65', then undone, and the rod 70, either at the same time as he withdraws the rod 70 completely, or by way of the strand 65'c which reemerges (for example by way of the lateral outlet 64a in FIG. 8).

It should be noted that both versions of FIGS. 11 and 15 allow progressive unknotting, only in one direction, of the tie surrounding the body forming a sleeve of the implant, from the distal end of the latter which emerges first during the installation in the implantation canal, which makes it possible to control the radial opening of the implant satisfactorily, even if the radial retention of the stent or stents with which it may moreover be provided were not controlled by a tie but only by the sheath 52, as long as the implant is contained therein.

It will also be noted that both the lacing of the retaining threads 65, 65' and their "unlacing" operate here in the same direction, preferably with evolution in two opposed directions (whether it is a question of bringing together towards a central area or moving away in the direction of the opposite ends of the implant).

It should also be noted that the tie(s) system of the invention could even be used on implants devoid of an armature of the "stent" type.

What is claimed is:

1. A system for repairing an anatomical duct of a patient in which a fluid circulates, said system comprising:
    an implant having a generally tubular body adapted for channeling the fluid along a major axis of the implant, the implant having a first configuration for being implanted in the duct and a second Configuration once implanted in the duct, the implant having an overall radial dimension with respect to the axis which is smaller when the implant is in the first configuration than when the implant is in the second configuration and the generally tubular body having a length along the axis; and
    a device for installing the implant in the duct, the device for installing comprising:

at least one retaining tie having a rigidity and configured to maintain the body of the implant substantially in the first configuration, the at least one retaining Lie forming a succession of loops passing at least partially around the body and extending at least over a major portion of its length to form a chain, said at least one retaining tie terminating towards a distal end of the implant in a distal knot or loop, and a flexible, elongated element for restraining, then releasing, the at least one retaining tie, the flexible, elongated element having a rectilinear cross section and sufficient rigidity so that a free distal end of the flexible, elongated element holds the distal knot or loop and the retaining tie in a predetermined position, the flexible, elongated element extending outside the body of the implant and at least over said major portion of its length, the flexible, elongated element being long enough to extend from outside the body of a patient to the distal end of the implant, the free distal end of the flexible, elongated element there locking the distal knot or loop to keep the implant in its first configuration until the flexible, elongated element is removed, whereupon the distal knot is released and thus the implant is able to assume its second configuration, wherein said at least one retaining tie loops substantially in a hairpin shape around the elongated element, passing periodically on one side thereof and then on the other while being disposed at least over the major portion of the length of the generally tubular body until said at least one retaining tie terminates in the releasable knot or loop substantially at the distal end of the elongated element, and wherein the rigidity of the elongated element is sufficiently greater than the rigidity of said at least one retaining tie that, when the implant is in the first configuration with the smaller overall radial dimension, the elongated element resists kinking, coiling, or other deformation which otherwise would result from shear stresses caused by the alternating passage of the at least one retaining tie around the elongated element.

2. The system according to claim 1, further comprising a sheath for placing the implant in position in the duct, the sheath having a distal end to be introduced deepest into the body of the patient to be treated, with the implant placed inside maintained in its first configuration.

3. The system of claim 1, wherein the flexible, elongated element is a metal rod.

4. The system of claim 1, wherein the flexible, elongated element is a plastic rod.

5. The system of claim 1, wherein the flexible, elongated element has a flattened cross-section.

6. A system for repairing an anatomical duct of a patient in which a fluid circulates, said system comprising:

an implant including a body having a generally tubular surface and adapted for channeling the fluid along a major axis of the implant, the implant having a first configuration for being implanted in the duct and a second configuration once implanted in the duct, the implant having an overall radial dimension with respect to the axis which is smaller when the implant is in the first configuration than when the implant is in the second configuration and the generally tubular body having a length along the axis; and a device for installing the implant in the duct, the device for installing comprising:

at least one retaining tie having a rigidity and configured to maintain the body of the implant substantially in the first configuration, the at least one retaining tie forming a succession of loops passing at least partially around the body and extending at least over a major portion of its length to form a chain, said at least one retaining tie terminating towards a distal end of the implant in a distal knot or loop, and a flexible, elongated element for restraining, then releasing, the at least one retaining tie, the flexible, elongated element having sufficient rigidity so that a distal end of the flexible, elongated element holds the distal knot or loop and the retaining tie in a predetermined position, the flexible, elongated element extending outside the body of the implant and at least over said major portion of its length, the flexible, elongated element being long enough to extend from outside the body of a patient to the distal end of the implant, the distal end of the flexible, elongated element there locking the distal knot or loop to keep the implant in its first configuration until the flexible, elongated element is removed, whereupon the distal knot is released and thus the implant is able to assume its second configuration, wherein, when the implant is in the first configuration, with the smaller overall radial dimension, the distal end of said elongated element is free, and up to said distal end, the elongated element is naturally continuously rectilinear, so that, beyond the body of the implant, said elongated element extends continuously in the axial extent of the tubular surface of said body, and the rigidity of the elongated element is sufficiently greater than the rigidity of said at least one retaining tie that the elongated element resists kinking, coiling, or other deformation which otherwise would result from shear stresses caused by the alternating passage of the at least one retaining tie around the elongated element.

7. A system for repairing an anatomical duct of a patient in which a fluid circulates, said system comprising:

an implant having a generally tubular body adapted for channeling the fluid along a major axis of the implant, the implant having a first configuration for being implanted in the duct and a second configuration once implanted in the duct, the implant having an overall radial dimension with respect to the axis which is smaller when the implant is in the first configuration than when the implant is in the second configuration and the generally tubular body having a length along the axis; and a device for installing the implant in the duct, the device for installing comprising:

at least one retaining tie having a rigidity and configured to maintain the body of the implant substantially in the first configuration, the at least one retaining tie forming a succession of loops passing at least partially around the body and extending at least over a major portion of its length to form a chain, said at least one retaining tie terminating towards a distal end of the implant in a distal knot or loop, and a flexible, elongated element for restraining, then releasing, the at least one retaining tie, the flexible, elongated element having sufficient rigidity so that a free distal end of the flexible, elongated element holds the distal knot or loop and the retaining tie in a predetermined position, the flexible, elongated element extending outside the body of the implant and at least over said major portion of its length, the flexible, elongated element being long enough to extend from outside the body of a patient to the distal end of the implant, the free distal end of the flexible, elongated element there locking the distal knot or loop to keep the implant in its first configuration until the flexible, elongated element is removed, whereupon the distal knot is released and thus the implant is able to assume its second configuration, wherein the flexible elongated element has a flattened cross section.

8. A system for repairing an anatomical duct of a patient in which a fluid circulates, said system comprising:

an implant including a body having a generally tubular surface and adapted for channeling the fluid along a major axis of the implant, the implant having a first configuration for being implanted in the duct and a second configuration once implanted in the duct, the implant having an overall radial dimension with respect to the axis which is smaller when the implant is in the first configuration than when the implant is in the second configuration and the generally tubular body having a length along the axis; and a device for installing the implant in the duct, the device for installing comprising:

at least one retaining tie having configured to maintain the body of the implant substantially in the first configuration, the at least one retaining tie forming a succession of loops passing at least partially around the body and extending to form a chain, said at least one retaining tie terminating in a knot or loop, and a flexible, elongated element for restraining, then releasing, the at least one retaining tie, the flexible, elongated element having sufficient rigidity so that a distal end of the flexible, elongated element holds the distal knot or loop and the retaining tie in a predetermined position, the flexible, elongated element extending outside the body of the implant and at least over said major portion of its length, the flexible, elongated element being long enough to extend from outside the body of a patient to the distal end of the implant, the distal end of the flexible, elongated element there locking the knot or loop to keep the implant in its first configuration until the flexible, elongated element is removed, whereupon the knot is released and thus the implant is able to assume its second configuration, a central catheter around which is disposed the implant, in the first configuration, wherein, when the implant is in said first configuration with the smaller overall radial dimension, the distal end of said elongated element is free, so that it is deprived of any fastening engagement with said internal catheter, and up to said distal end, the elongated element is naturally continuously rectilinear, so that beyond the body of the implant, said elongated element extends continuously in the axial extent of the tubular surface of said body, and is thus free from penetrating in said internal catheter.

* * * * *